(12) United States Patent
Edwards, Jr. et al.

(10) Patent No.: US 8,450,349 B2
(45) Date of Patent: May 28, 2013

(54) LONG ACTING DUAL RELEASE PRODUCT CONTAINING CARBINOXAMINE AND PSEUDOEPHEDRINE

(75) Inventors: Robert J. Edwards, Jr., Parkland, FL (US); Chih-Ting Huang, Taoyuan (TW); Nam-Mew Pui, Taipei (TW)

(73) Assignee: E5 Pharma LLC, Coral Springs, FL (US)

( * ) Notice: Subject to any disclaimer, the term of this patent is extended or adjusted under 35 U.S.C. 154(b) by 282 days.

(21) Appl. No.: 12/208,576

(22) Filed: Sep. 11, 2008

(65) Prior Publication Data

US 2009/0092670 A1    Apr. 9, 2009

Related U.S. Application Data

(60) Provisional application No. 60/971,984, filed on Sep. 13, 2007.

(51) Int. Cl.
- *A61K 31/44* (2006.01)
- *A01N 43/00* (2006.01)
- *C07D 213/40* (2006.01)

(52) U.S. Cl.
CPC .................. *C07D 213/40* (2013.01)
USPC ............................. 514/357; 514/282; 514/161

(58) Field of Classification Search
None
See application file for complete search history.

(56) References Cited

U.S. PATENT DOCUMENTS

| 6,051,585 A | 4/2000 | Weinstein et al. |
| 6,613,357 B2 | 9/2003 | Faour et al. |
| 2004/0253311 A1* | 12/2004 | Berlin et al. .................. 424/472 |

OTHER PUBLICATIONS

Beale et al., J. Allergy, 1954, 25(5), pp. 521-524.*
Ebadi, Manuchair; "CRC Desk Reference of Clinical Pharmacology," 1998, pp. 119 and 322.*
FDA-Approved Label for Carbinoxamine Maleate (Boca Pharamacal, Jun. 2009), from http://dailymed.nlm.nih.gov/dailymed/lookup.cfm?setid=1741b4f2-af49-43fe-8319-7b8a38fa25d2, last accessed Feb. 8, 2013.

* cited by examiner

*Primary Examiner* — Brian Gulledge
(74) *Attorney, Agent, or Firm* — Arnall Golden Gregory LLP; Clark G. Sullivan

(57) ABSTRACT

Provided are oral dosage forms that contain carbinoxamine in an immediate release format, and pseudoephedrine in a prolonged release format. The biphasic oral dosage forms may also contain other active ingredients in combination with carbinoxamine, including other decongestants, antitussives, analgesics and expectorants.

16 Claims, 9 Drawing Sheets

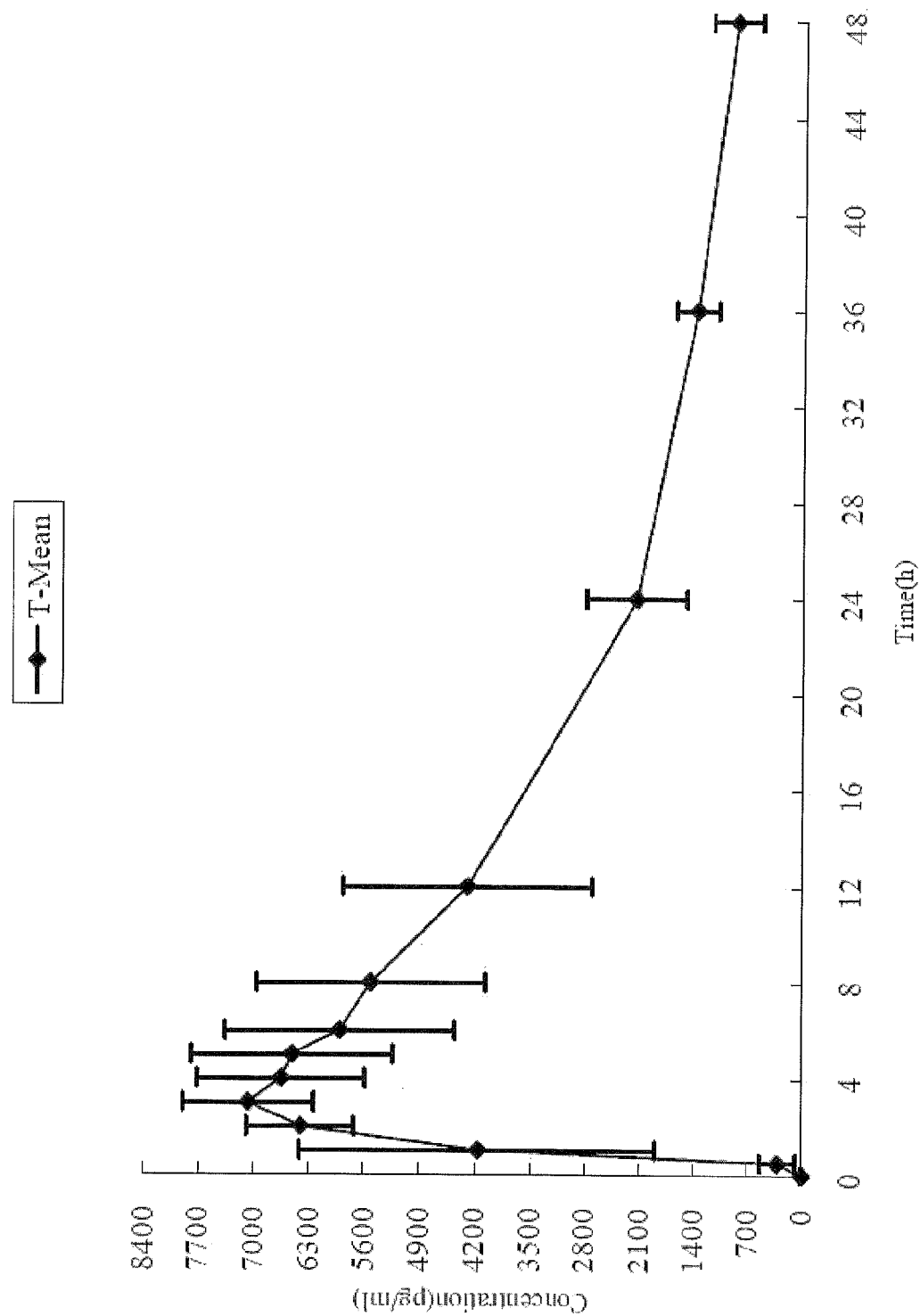
Figure 1(A). Mean plasma concentration-time profile of carbinoxamine after administering test drug in fasted state from time 0 to time 48 hours: Linear ordinate.

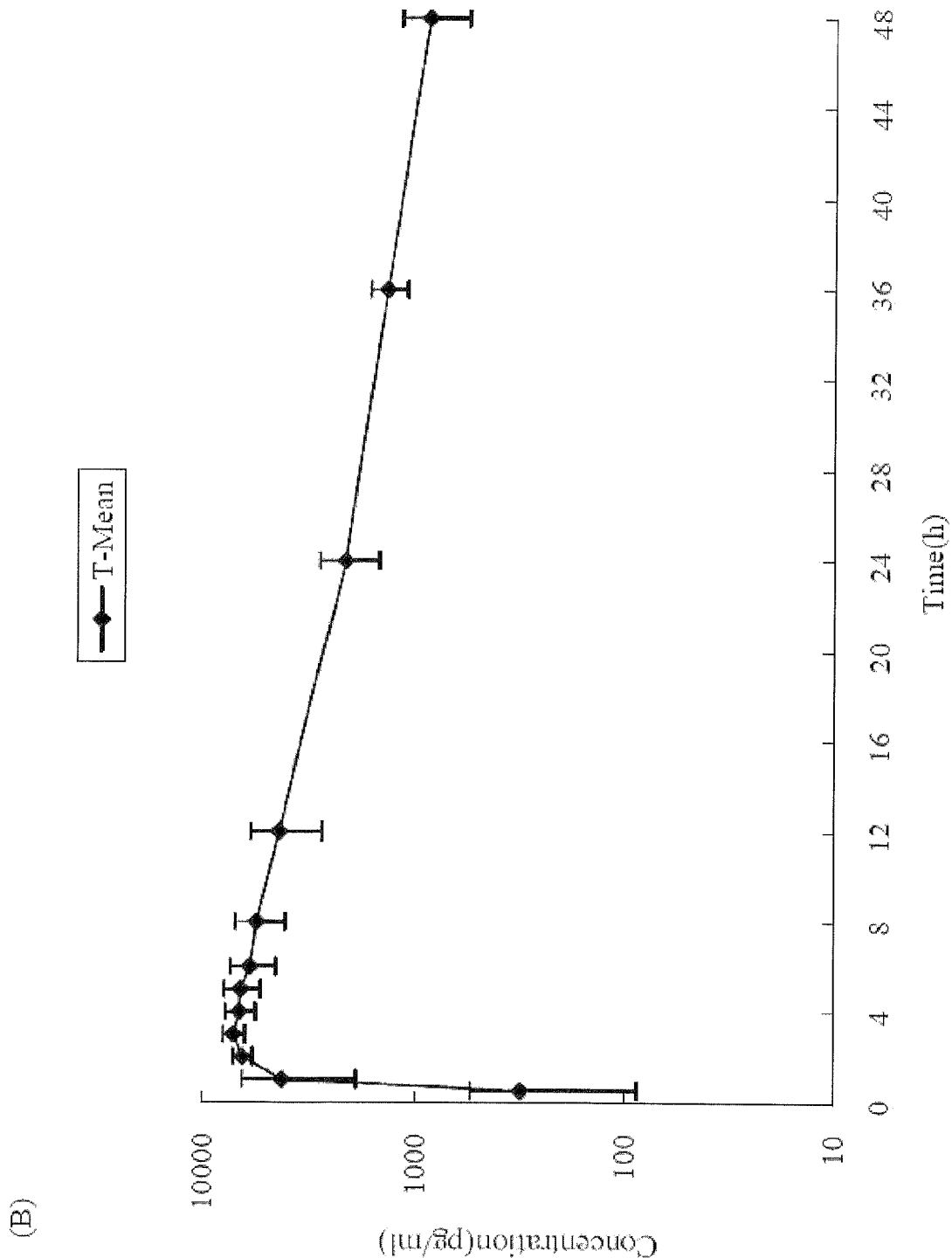
Figure 1(B). Mean plasma concentration-time profile of carbinoxamine after administering test drug in fasted state from time 0 to time 48 hours: Log-Linear ordinate.

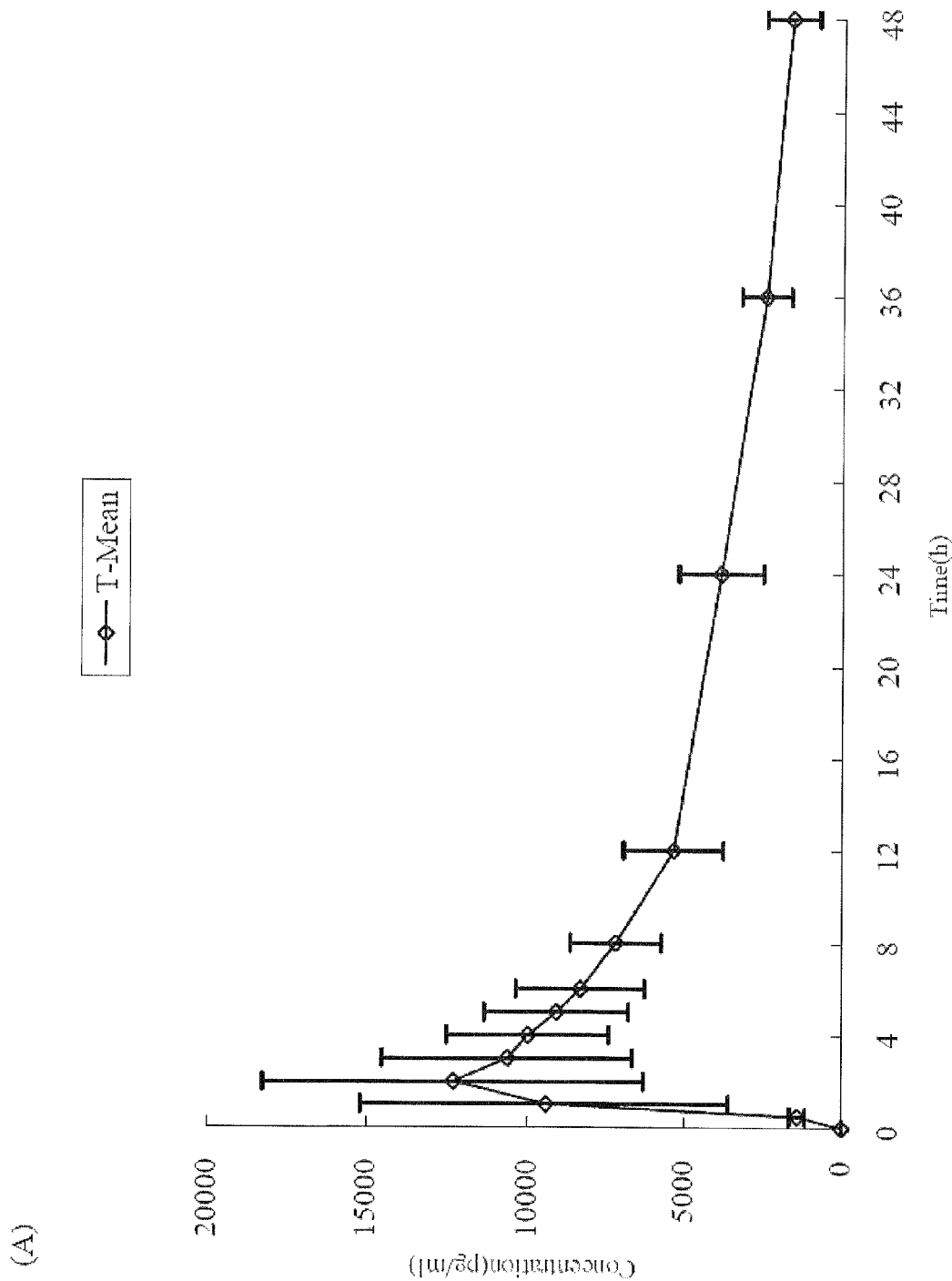
Figure 2(A). Mean plasma concentration-time profile of carbinoxamine after administering test drug in non-fasted state from time 0 to time 48 hours: Linear ordinate.

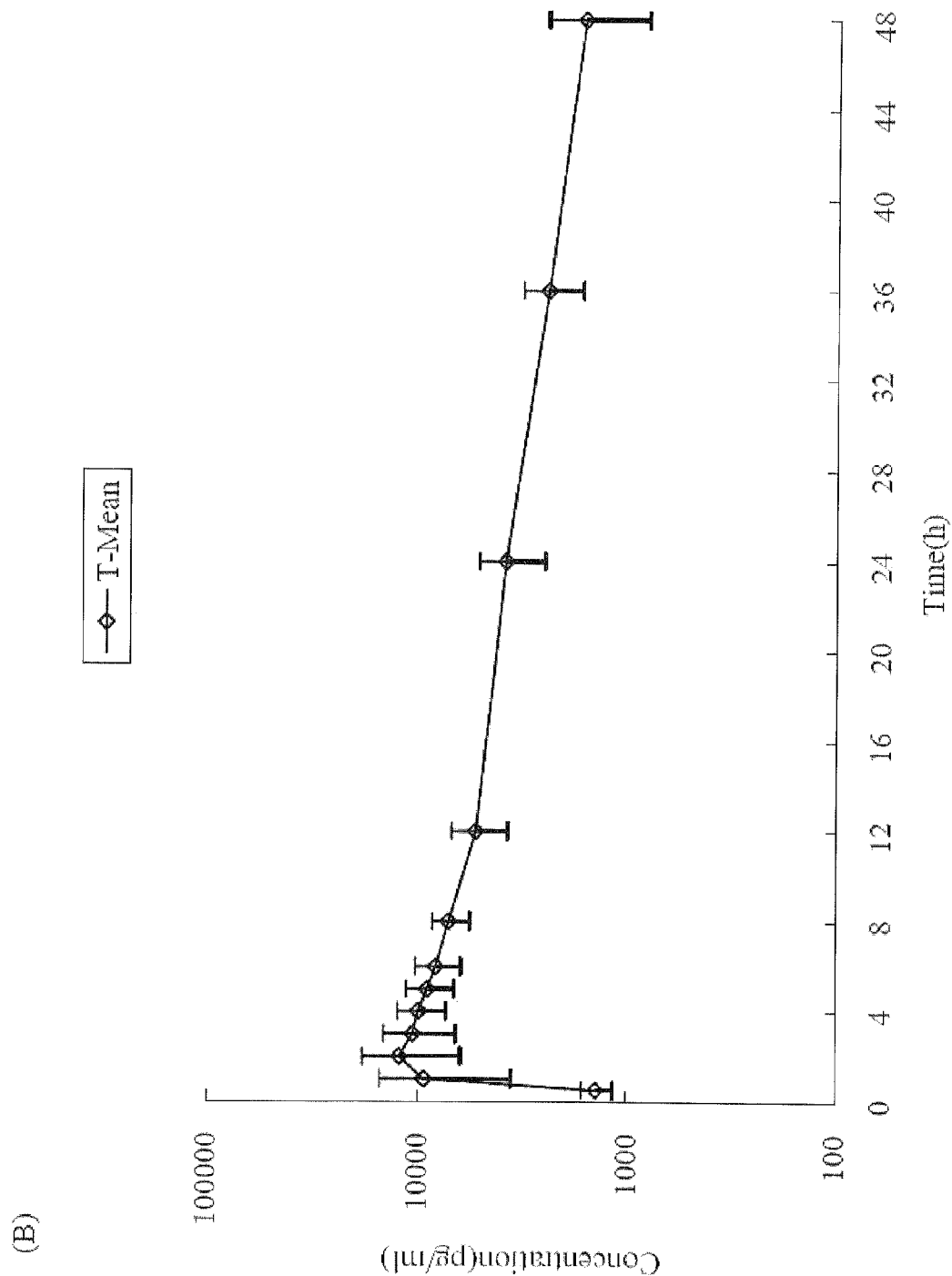
Figure 2(B). Mean plasma concentration-time profile of carbinoxamine after administering test drug in non-fasted state from time 0 to time 48 hours: Log-Linear ordinate.

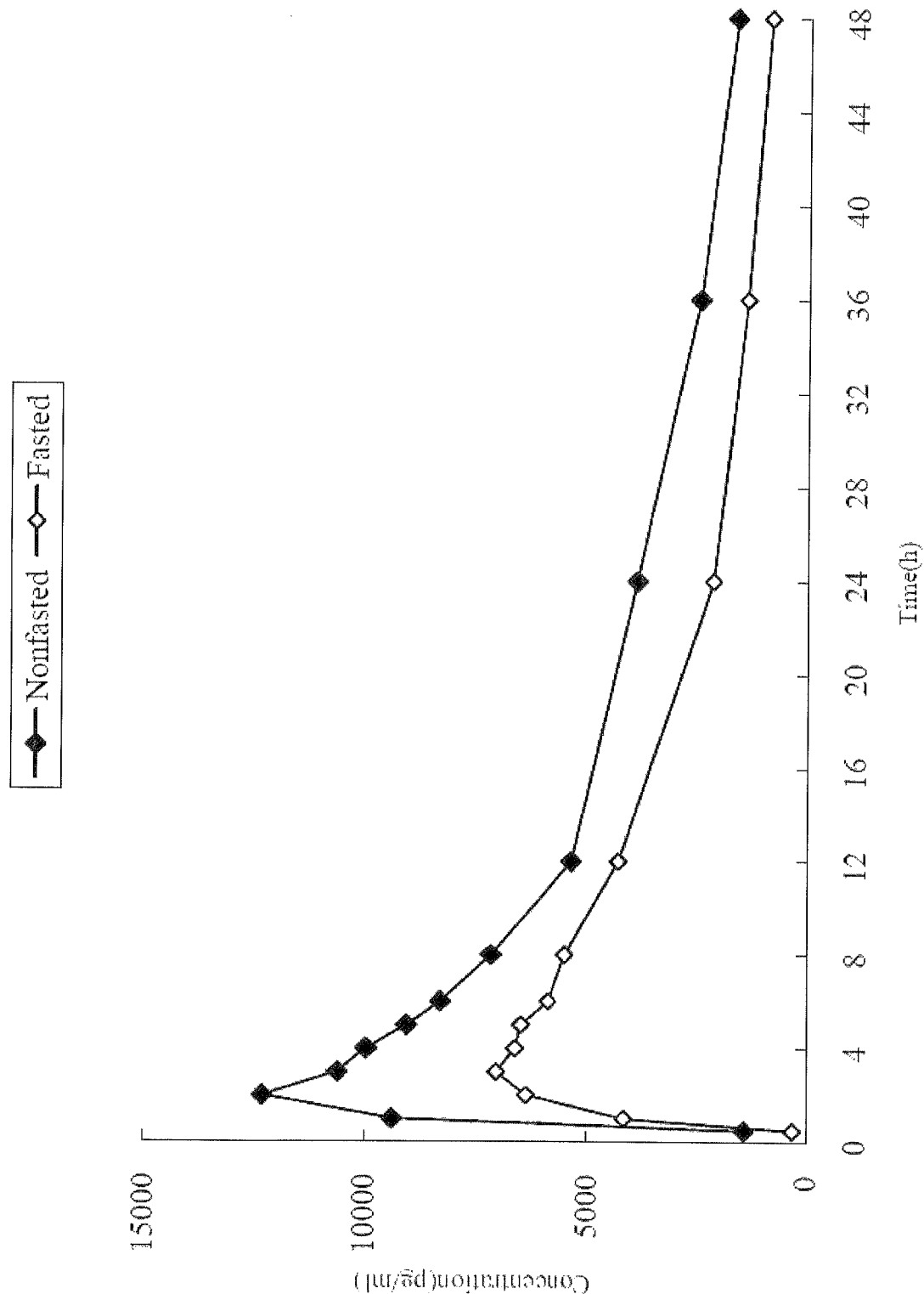
Figure 3(A). Mean plasma concentration-time profile of carbinoxamine administered under nonfasted and fasted state from time 0 to 48 hours: Linear ordinate.

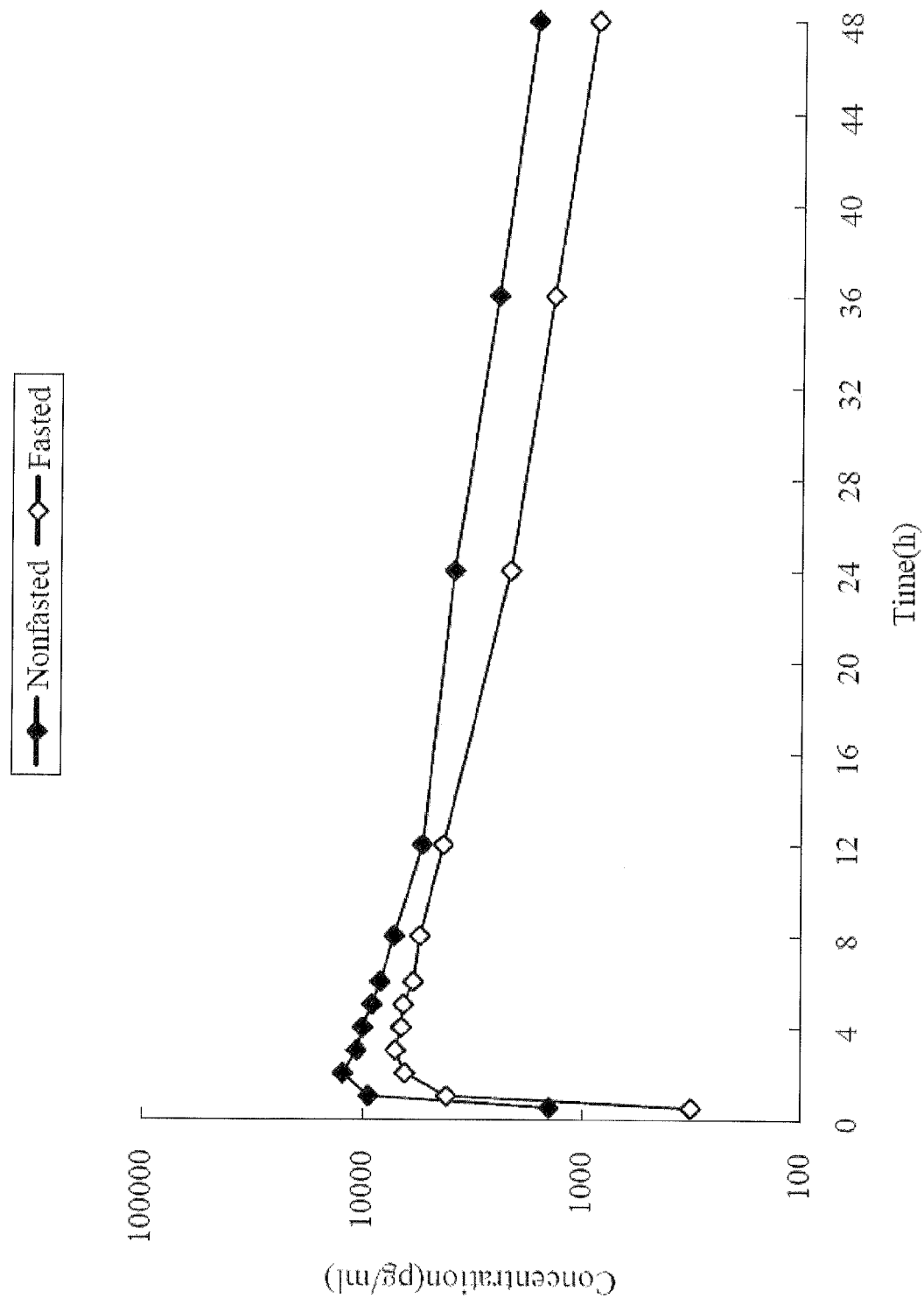
Figure 3(B). Mean plasma concentration-time profile of carbinoxamine administered under nonfasted and fasted state from time 0 to 48 hours: Log-Linear ordinate.

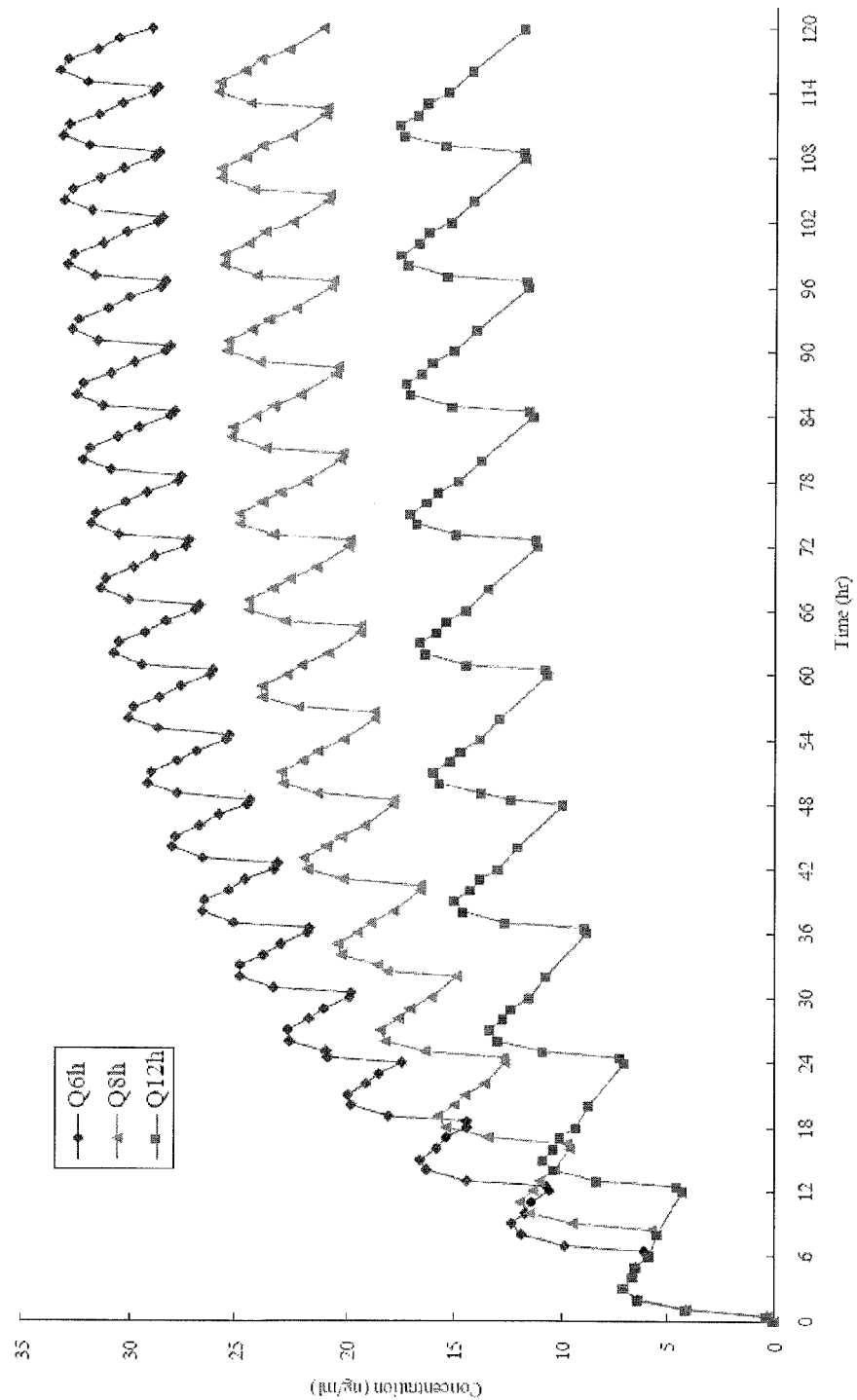
Figure 4. Simulated steady-state plasma concentration-time profiles of carbinoxamine. Top line (Q6h); Middle line (Q8h); Bottom line (Q12h).

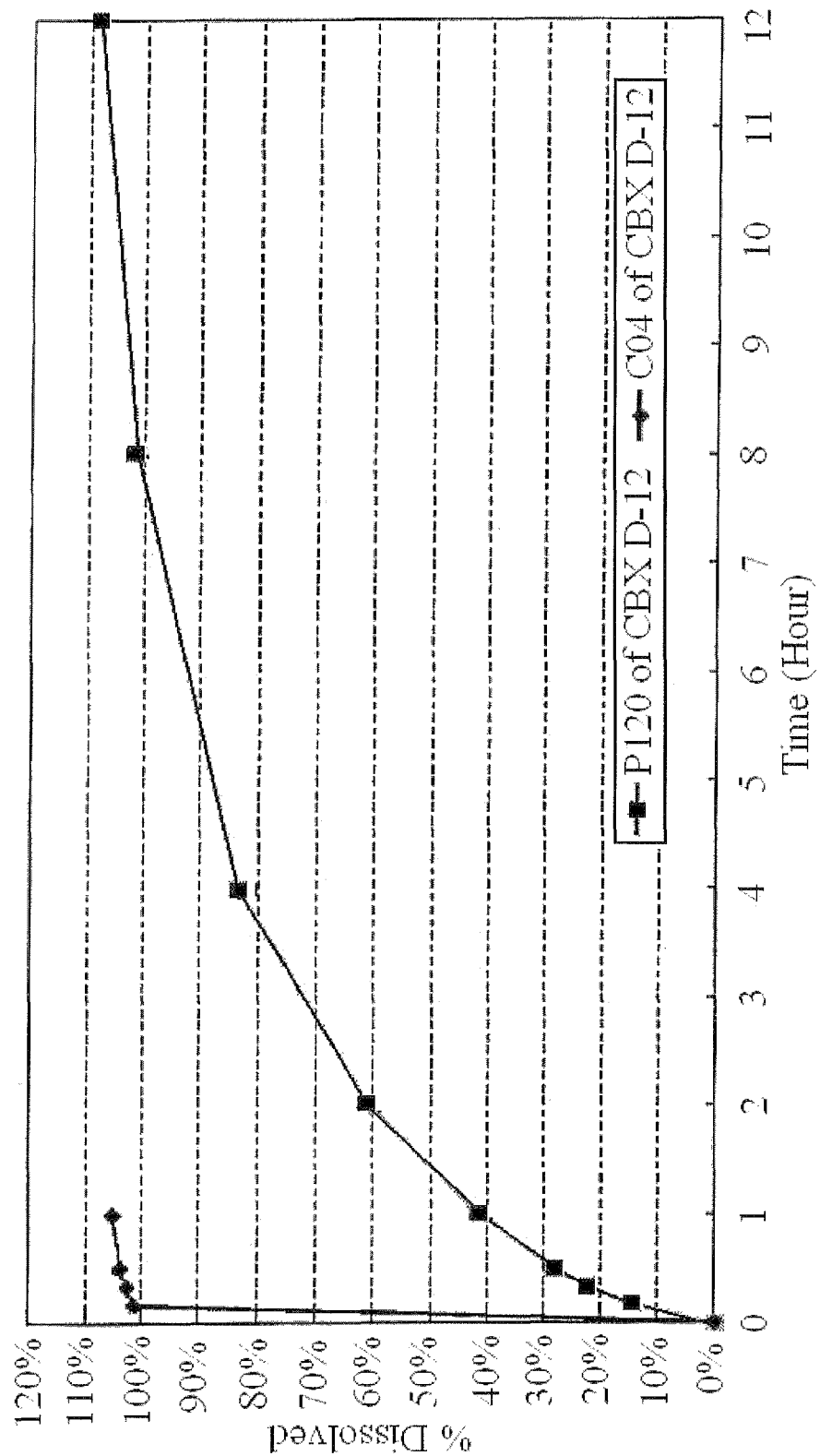
FIGURE 6. Carbinoxamine Maleate 4mg (IR) & Pseudoephedring HCl 120mg (12-hours SR) BilayerTable 0.1N NCl, 900 mL; Apparatus 2, 50rpm: Sinker

LONG ACTING DUAL RELEASE PRODUCT CONTAINING CARBINOXAMINE AND PSEUDOEPHEDRINE

FIELD OF THE INVENTION

The present invention relates to methods and compositions for the treatment of allergic rhinitis.

BACKGROUND OF THE INVENTION

Carbinoxamine maleate is an antihistamine with anticholinergic (drying) and sedative effects. The molecule is chemically known as 2-[(4-chlorophenyl)-2-pyridinylmethoxy]-N,N-dimethylethanamine (Z)-2-butenedioate (1:1), and has the following chemical structure:

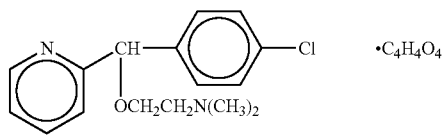

The compound was originally developed in the early 1950's by McNeil Laboratories. Beale et al., *Clistin® Maleate: Clinical Appraisal of a New Antihistaminic, Jnl. Allergy* 1954, 25:521-524. The product is currently marketed by Pamlab under the Palgic® brand as immediate release tablets and oral solution, for the treatment of seasonal allergic rhinitis. The recommended dose is 4 to 8 mg three or four times daily, which equates to a daily dose of from 12 to 32 mg. Teamm Pharmaceuticals markets a 12 hr. prolonged release carbinoxamine tablet as Histex CT that contains 8 mg of carbinoxamine maleate.

The pharmacokinetics of carbinoxamine maleate have been reported in the literature. Stoekis et al., *Arzneim.-Forsch* 1992, 42(12):1478-81, studied the bioavailability of an 8 mg aqueous solution of carbinoxamine and an 8 mg retard capsule of carbinoxamine. The authors reported a $C_{max}$ of 24 and 16.9 ng/ml, $T_{max}$ of 3 and 8 hours, and a half-life of 10.6 and 14.5 hours for the solution and capsule, respectively. Stockis et al., *Arzneim.-Forsch* 1995, 45(9) 1009-1012, studied the bioavailability of a 4 mg retard capsule after a single and successive administrations, and reported a $C_{max}$ of 4.5 and 13.5, a $T_{max}$ of 6.2 and 4.8, and a half life of 30 and 22 for the 4 mg capsule after single and successive administrations, respectively.

Pseudoephedrine hydrochloride is an orally active sympathomimetic amine that exerts a decongestant action on the nasal mucosa. The molecule has the chemical name [S-(R*,R*)]-α-[1-(methylamino)ethyl]-benzenemethanol hydrochloride and the following chemical structure:

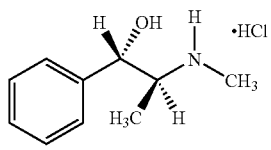

Pseudoephedrine has been shown to have a mean elimination half-life of 4-6 hours which is dependent on urine pH. The elimination half-life is decreased at urine pH lower than 6 and may be increased at urine pH higher than 8.

Dosage forms that combine pseudoephedrine with an antihistamine such as loratadine, cetirizine, fexofenadine, terfenadine, acrivastine or astemizole are known. In general, the amount of pseudoephedrine and antihistamine in these formulations is derived independently, based upon known dosing amounts for the individual ingredients. For example, Allegra-D® (12 hr) combines 60 mg of fexofenadine hydrochloride, which is the same dose employed in single ingredient 12 hr fexofenadine formulations, with 120 mg of pseudoephedrine, which is the same dose employed in 12 hr. single ingredient sustained release pseudoephedrine formulations. Similarly, Claritin D (12 hr) combines 5 mg of loratadine, which is 1/2 of the dose employed in single ingredient 24 hr loratadine formulations, with 120 mg of pseudoephedrine.

U.S. Pat. No. 6,051,585 to Weinstein et al. discloses a combination formulation containing pseudoephedrine, with limited duration of action, and an antihistamine for treating seasonal allergic rhinitis. U.S. Pat. No. 6,613,357 to Faour et al. discloses a combination osmotic device containing pseudoephedrine and an antihistamine for treating seasonal allergic rhinitis.

There exists a continuing need for effective prolonged release combination dosage forms for the relief of symptoms associated with allergic rhinitis and other respiratory conditions.

SUMMARY OF INVENTION

The current invention provides a combination carbinoxamine-based dosage form having a surprisingly small amount of carbinoxamine in the product but a prolonged twelve hour duration of action. The product releases carbinoxamine almost immediately upon ingestion as an immediate release component; and pseudoephedrine or another pharmaceutically active agent over an extended period of time. The dosage form requires only four milligrams of carbinoxamine for twelve hours of effect, and is particularly well adapted for successive twelve hour administrations, due to the surprising steady state carbinoxamine pharmacokinetics that are observed.

Thus, contrary to prior art carbinoxamine products such as Histex® CT, which teach that carbinoxamine should be formulated in a prolonged release format where twelve hour relief is sought, the inventors have discovered that carbinoxamine can provide twelve hours of relief when administered as an immediate release component, especially when combined with prolonged release pseudoephedrine and dosed at steady state.

Contrary to prior art products such as Palgic and Histex CT, which teach that higher doses of carbinoxamine are needed for therapeutic effect over a twelve hour period, or products such as Allegra® D and Claritin® D, which teach that the antihistamine in a twelve hour product should be equipotent to the total amount of antihistamine administered in IR format over 12 hours, the inventors have discovered that only four milligrams are needed for twelve hour relief, especially when combined with prolonged release pseudoephedrine and dosed at steady state.

These discoveries for the first time enable a twelve-hour dosage form that combines the antihistamine and anticholinergic effects of carbinoxamine in an immediate release format, with the decongestant properties of pseudoephedrine in a prolonged release format, or another suitable pharmaceutical agent. Therefore, in a first embodiment, the invention provides a pharmaceutical dosage form for providing fast and extended relief from symptoms associated with allergic rhinitis comprising: (a) a therapeutically effective amount of carbinoxamine or a pharmaceutically acceptable salt thereof in an immediate release format; and (b) a therapeutically effective amount of a second pharmaceutically acceptable agent selected from a decongestant, an antitussive, an analgesic or an expectorant in a prolonged release format; wherein said therapeutically effective amounts of said carbinoxamine or carbinoxamine salt and said second agent are sufficient to provide relief from said symptoms for at least twelve hours. In a preferred embodiment, the second agent comprises pseudoephedrine hydrochloride.

In another embodiment, the invention provides methods of treatment by administering the pharmaceutical dosage form of the present invention in successive twelve-hour administrations. In one preferred embodiment, the carbinoxamine or carbinoxamine salt is present in an amount sufficient to produce a mean carbinoxamine plasma concentration during a second or subsequent administration of more than 25% greater than the mean carbinoxamine plasma concentration produced during an initial administration.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE FIGURES

The figures are illustrative only and are not required for enablement of the inventions disclosed herein.

FIG. 1 is a mean plasma concentration-time profile of carbinoxamine after administering a 4 mg carbinoxamine maleate immediate release tablet in the fasted state from time 0 to time 48 hours. Graph (A) is the linear ordinate; graph (B) is the log-linear ordinate.

FIG. 2 is a mean plasma concentration-time profile of carbinoxamine after administering a 4 mg carbinoxamine maleate immediate release tablet in the non-fasted state from time 0 to time 48 hours. Graph (A) is the linear ordinate; graph (B) is the log-linear ordinate.

FIG. 3 is an overlay of mean plasma concentration-time profiles of carbinoxamine administered under nonfasted and fasted conditions from time 0 to 48 hours. Graph (A) is an overlay in the linear ordinates for the two conditions; graph (B) is an overlay in the log-linear ordinates for the two conditions.

FIG. 4 is a simulated steady-state plasma concentration-time profile for an immediate release 4 mg carbinoxamine maleate formulation. The top line reflects Q6h administration; the middle line reflects Q8h administration; the bottom line reflects Q12h administration.

FIG. 6 shows the in vitro dissolution profile of tablets manufactured according to Example 1 are established using the Apparatus TI of the United States Pharmacopoeia. 1 dissolution media is employed: 900 ml 0.1N hydrochloric acid (pH=2) and maintained at 37+/−0.5° C. Stirring is by the paddle method (50 rpm). Dissolution of pseudoephedrine HCl and carbinoxamine maleate are plotted versus time.

DETAILED DESCRIPTION

Definitions and Use of Terms

Figure 5:
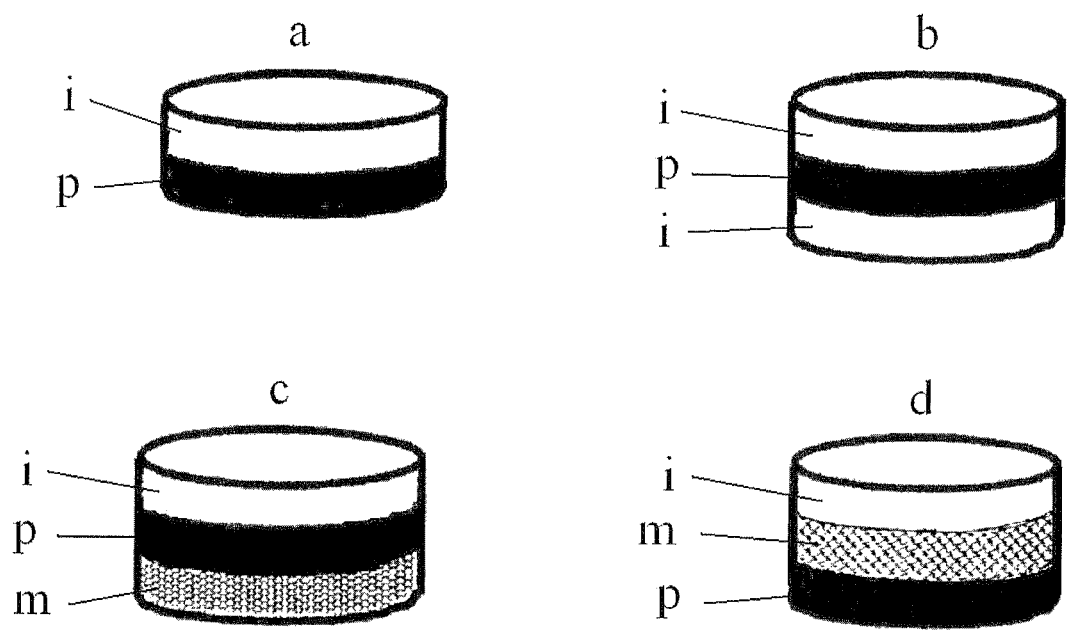
FIG. 5 shows four bilayer and multilayer tablet configurations that can be made according to the present invention: (a) a bilayer tablet consisting of one immediate release layer and one prolonged release layer; (b) a triple layer tablet consisting of two outer immediate release layers and one inner prolonged release layer; (c) a triple layer tablets consisting of an outer immediate release layer, an inner prolonged release layer, and an outer layer not containing active substance, modulating the release profile; and (d) a triple layer tablets consisting of an outer immediate release layer, an outer prolonged release layer, and an inner layer not containing active substance, modulating the release profile.

The term "immediate release" as used herein refers to a dosage form adapted to release at least 80% or 90% of an active pharmaceutical ingredient in 60 minutes or less when measured in a type II dissolution apparatus, according to <711> and <724> of the U.S. Pharmacopoeia (2005 USP/NF) in 0.1N hydrochloric acid buffer (pH=2) at 37° C.

In a preferred embodiment, at least 80%, 90% or 100% is dissolved in no more than 45 minutes. In alternative embodiments, at least 80%, 90% or 100% are dissolved in no more than 45 or 30 minutes. Stirring preferably occurs using the paddle method at 50 rpm.

The term "prolonged release" as used herein refers to a dosage form adapted to release:

(i) no more than about 40%, or approximately 40%, of an active pharmaceutical ingredient in from about 30 to about 90 minutes, or from about 45 to about 75 minutes; and (ii) at least about 80%, or about 80%, of said active agent in from about two to about six hours, or from about three to about five hours, when measured in a type II dissolution apparatus according to the <711> and <724> of the U.S. Pharmacopoeia (2005 USP/NF) in 0.1N hydrochloric acid buffer (pH=2) at 37° C. Stirring preferably occurs using the paddle method at 50 rpm.

The term carbinoxamine includes carbinoxamine and its pharmaceutically acceptable salts, including carbinoxamine maleate, unless the context suggests otherwise. Likewise, the term pseudoephedrine includes pseudoephedrine and its pharmaceutically acceptable salts, including pseudoephedrine hydrochloride, unless the context suggests otherwise.

When doses are given for a drug and its salt, it will be understood that the calculated dose is based on the molecular weight of the active pharmaceutical ingredient, which includes the cationic and anionic species in the case of a salt, and just the base when the active principle is not present as a salt.

When ranges are given by specifying the lower end of a range separately from the upper end of the range, it will be understood that the range can be defined by selectively combining any one of the lower end variables with any one of the upper end variables that is mathematically possible.

When used herein the term "about" will compensate for variability allowed for in the pharmaceutical industry and inherent in pharmaceutical products, such as differences in product strength due to manufacturing variation and time-induced product degradation. The term allows for any variation which in the practice of pharmaceuticals would allow the product being evaluated to be considered bioequivalent to the recited strength.

Preferred Doses and Pharmacokinetics

The present invention provides a novel method of treatment that incorporates carbinoxamine in an immediate release format, and one or more other active ingredients in a prolonged release format. The methods and dosage forms are particularly directed toward the treatment of symptoms associated with allergic rhinitis and the common cold, such as bronchial congestion, runny nose, itchy eyes, pain, sneezing and coughing, for periods of twelve hours and greater from a single dose. The methods are also well adapted for the treatment of persistent symptoms that persist for two or more days, and that require successive dosing of medication every twelve hours.

The use of an immediate release format for the carbinoxamine—for a twelve hour dose—was arrived at after an intensive investigation and study which showed that immediate release carbinoxamine tablets, when administered repeatedly so that steady state can be reached, exhibit a pharmacokinetic profile similar to prolonged release products. The use of a low dose over twelve hours—of only 4 mg—was also arrived at from this multi-dose steady state testing, which revealed steady state plasma concentrations from twelve hour multiple dosing that were nearly double the concentrations observed from a single dose. Neither of these parameters could have been predicted from prior art reports of the pharmacokinetics of carbinoxamine maleate.

Therefore, in one embodiment the invention provides a method of providing relief from symptoms associated with allergic rhinitis comprising administering to a human patient a single pharmaceutical dosage form comprising:
  i) a therapeutically effective amount of carbinoxamine or a pharmaceutically acceptable salt thereof in an immediate release format, preferably adapted to release at least 80% of said carbinoxamine or carbinoxamine salt in 60 minutes or less when measured in a type II dissolution apparatus according to the U.S. Pharmacopoeia in 0.1N hydrochloric acid buffer (pH=2) at 37° C.; and
  ii) a therapeutically effective amount of a pharmaceutically acceptable decongestant (preferably pseudoephedrine) in a prolonged release format, preferably adapted to release no more than 50% of said decongestant in 60 minutes or less, and at least 75% of said decongestant in eight hours or less, when measured in a type II dissolution apparatus according to the U.S. Pharmacopoeia in 0.1N hydrochloric acid buffer (pH=2) at 37° C.

In a preferred embodiment, the dosage form is administered twelve hours after the first administration, and optionally every twelve hours thereafter for two or more days, until the symptoms of allergic rhinitis have subsided or abated.

In another aspect, the invention relates to the actual dosage form administered, and in this embodiment the invention provides an orally administered pharmaceutical dosage form comprising:
  a) a therapeutically effective amount of carbinoxamine or pharmaceutically acceptable salt thereof in an immediate release format, preferably adapted to release at least 80% of said carbinoxamine or carbinoxamine salt in 60 minutes or less when measured in a type II dissolution apparatus according to the U.S. Pharmacopoeia in 0.1N hydrochloric acid buffer (pH=2) at 37° C.; and
  b) a therapeutically effective amount of a pharmaceutically acceptable decongestant (preferably pseudoephedrine) in a prolonged release format adapted to release no more than 50% of said decongestant in 60 minutes or less, and at least 75% of said decongestant in eight hours or less, when measured in a type II dissolution apparatus according to the U.S. Pharmacopoeia in 0.1N hydrochloric acid buffer (pH=2) at 37° C.

While the preferred dose for practicing the invention is 4 or 6 mg of carbinoxamine, it will be understood that other doses are therapeutically effective and can be used to practice the invention. Thus, a therapeutically effective amount of carbinoxamine ranges from 1 mg to 16 mg every twelve hours. A preferred range of doses is from about 2 to about 8 mg or from 4 to about 6 mg every twelve hours. A particularly preferred dose is 4 or 6 mg (preferably carbinoxamine maleate, based on the weight of the maleate salt).

When administered as a 4 mg immediate release dose, the carbinoxamine preferably produces a mean peak plasma concentration ranging from about 4 or 5 ng/ml to about 20 or 15 ng/ml. When administered in the fasted state, the 4 mg immediate release dosage form preferably produces a mean peak plasma concentration of from about 4 or 8 to about 20 or 15 ng/ml. When administered in a nonfasted state, the 4 mg immediate release dosage form preferably produces a mean peak plasma concentration of from about 5 or 9 ng/ml to about 20 or 15 ng/ml. These figures can be normalized based on a 4 mg carbinoxamine dose, and extrapolated when other doses of carbinoxamine are employed. Mean peak plasma concentrations are preferably observed in greater than 2.0 or 2.5 hours, and less than 4.0 or 3.5 hours. The carbinoxamine preferably displays a half-life of greater than 12 or 15 hours, and less than 22 or 20 hours.

Steady state pharmacokinetics for the carbinoxamine should be contrasted with single dose pharmacokinetics, as simulated in FIG. 4. In a preferred embodiment when the administration is repeatedly administered over a twelve hour dosing regimen, and steady state plasma concentrations are preferably reached, mean and mean peak plasma concentrations of carbinoxamine should be more than 25%, 50%, or even 75% greater than the mean and/or peak concentrations observed from the initial dose of carbinoxamine, when administered in the fasted and/or non-fasted state (preferably no more than 200% or 300% greater).

Therefore, in another embodiment the therapeutically effective amounts of carbinoxamine or carbinoxamine salt and decongestant are sufficient to provide symptomatic relief for at least twelve hours; and the carbinoxamine or carbinoxamine salt is present in an amount sufficient to produce a mean carbinoxamine plasma concentration when administered a second, third, fourth, fifth, or sixth time, or once steady state is reached, of more than 25%, 50%, or 75% greater than the mean carbinoxamine plasma concentration produced during the initial administration.

While the preferred twelve-hour dose of pseudoephedrine is 120 mg, it will be understood that other doses can be used to practice the invention and that a therapeutically effective amount of pseudoephedrine usually ranges from about 60 to about 240 mg every twelve hours. A preferred range of doses is from about 90 to about 150 mg every twelve hours. A particularly preferred dose is about 120 mg (preferably as pseudoephedrine hydrochloride based on the weight of the hydrochloride salt).

When administered as a single 120 mg twelve-hour prolonged release dose, the pseudoephedrine preferably produces a mean peak plasma concentration ($C_{max}$) of greater than about 180, 190 or 200 ng/ml, and less than about 400, 300, 250 or 210 ng/ml, in any combination of endpoints. The 120 mg dose preferably reaches a mean peak plasma concentration in greater than 3, 4, or 5 (preferably 4) hours post-dose, and less than 9, 8 or 7 (preferably 8) hours post-dose, in any combination of endpoints, most preferably in about 6 hrs post-dose, when a single dose is administered. When successive doses are administered every twelve hours and steady state is reached, the mean peak pseudoephedrine concentration will preferably exceed 200, 250 or 300 ng/ml (preferably 200), and be less than 450, 400, or 350 ng/ml (preferably 400), in any combination of endpoints. These figures can be normalized based on a 120 mg pseudoephedrine dose, and extrapolated when other doses of pseudoephedrine are employed. The mean peak plasma concentration at steady state will preferably be observed in greater than 3 or 4 hours post-dose, and less than 8 or 7 hours post-dose, most preferably in about 6 hours.

Other Combinations with Carbinoxamine

In alternative embodiments a twelve hour dose of carbinoxamine in an immediate release format can be combined with other agents useful for treating symptoms of allergic rhinitis or the common cold, including other decongestants, antitussives, expectorants and analgesics. These other agents may be included in the dosage form as an alternative to the pseudoephedrine, or in combination with the pseudoephedrine, but will almost always be present in a prolonged release format for providing twelve hours of release, and will always be present in a therapeutically effective dose. In a preferred embodiment, therefore, these alternative agents are present in a prolonged release format adapted to release no more than 50% of said second agent in 60 minutes or less, and at least 75% of said second agent in eight hours or less, when measured in a type II dissolution apparatus according to the U.S. Pharmacopoeia in 0.01 M hydrochloric acid buffer at 37° C.

Thus, the dosage form may further or alternatively comprise:
- Phenylephrine, in an amount of from about 5 to about 20 mg;
- An antitussive such as codeine (preferably as codeine phosphate) or dihydrocodeine (preferably as dihydrocodeine bitartrate), in an amount of from about 30 to about 150 mg, or dextromethorphan (preferably as the hydrobromide) in an amount of from about 5 or 10 mg to about 20 or 15 mg, in any combination of endpoints.
- An expectorant such as guaifenesin, preferably in an amount of from about 400 to about 1500 mg, or from about 600 to about 1200 mg;
- An analgesic such as naproxen, acetaminophen, ibuprofen, or aspirin, preferably for naproxen in an amount of from about 250 to about 750 mg, or from about 375 to about 500 mg; for acetaminophen in an amount of from about 250 to about 1000 mg, or from about 400 to about 800 mg; for ibuprofen and aspirin in an amount of from about 200 to about 1000 mg, or from about 400 to about 800 mg.

Drug Formats and Formulations

Dosage forms of the current invention include capsules, tablets, multilayer tablets, and multicoated tablets. The immediate release entity may be present as a single pharmaceutical immediate release unit like for example an immediate release tablet or pellet, or several such units formulated into a capsule or a tablet; as an immediate release matrix in a tablet; as an immediate release layer that can be incorporated in a multilayer tablet; or as an immediate release coating layer in a multicoated tablet or pellet.

The prolonged release entity may be present as a pharmaceutical prolonged release unit such as, for example, a prolonged release tablet or pellet, or several such units formulated into a capsule or a tablet; as a prolonged release layer that can be incorporated in a multilayer tablet; as a prolonged release core or a prolonged release coating layer in a multicoated tablet; or as prolonged release pellets within a disintegrating tablet.

Various formulations may be used to prepare these dosage forms, as described below:

A Capsule Comprising One or More Immediate Release Tablets and One or More Prolonged Release Tablets:

Immediate release tablets may be prepared by direct compression of mixtures of the drug or salts thereof with diluents, such as microcrystalline cellulose, mannitol, sorbitol, and lactose. Other functional excipients such as disintegrants and lubricants can be added. Choice of these functional excipients as well as diluent is well known in the art. Alternatively tablets may be prepared by granulation with water of a mixture of the drug or salts thereof with suitable diluents, disintegrant and binding polymer; calibration and drying of the granulate addition of a lubricant, followed by compression on a tableting machine. The methods used are those generally described in the pharmaceutical literature, see for example, B. B. Sheth, F. J. Bandelin and R. J F. Shangraw, Compressed Tablets, in Pharmaceutical Dosage Forms: Tablets, Vol 1. edited by H. A. Lieberman and L. Lachman, Dekker N.Y. (1980).

Prolonged release tablets can be prepared by coating immediate release tablets with a diffusion limiting polymer coating. Suitable polymers can be chosen among ethyl cellulose, methyl methacrylate copolymers, such as Eudragit® RS, Eudragit® RL, Eudragit® NE commercialized by Rohm Pharma. Coating methods can consist in spraying a solution of the polymer on the tablets, either in a pan coater or a fluid bed coating apparatus. The solvent may be organic or aqueous, depending on the nature of the polymer used. Coating methods are described in the following works: J. M. Bakan, Microencapsulation, in L. Lachman, H. Lieberlmman and J. L. Kanig (Eds.) The Theory and Practice of Industrial Pharmacy, Lea & Febinger, Philadelphia, USA, 1986; J. M. McGinity, Aqueous polymer coatings for Pharmaceutical Dosage Forms, Dekker N.Y., 1989. Alternatively prolonged release tablets can be prepared by incorporating matrix-forming excipients into the formulation, and omitting disintegrants. Such matrix-forming excipients may be hydrophilic polymers, which include hydroxypropylmethylcellulose, hydroxymethyleellulose, hydroxyethylcellulose, and which swell in contact with aqueous liquids, and control release of the drug by diffusion through the swollen polymer network, and are incorporated at a level between 10 and 30% by weight with respect to that of the prolonged release tablet.

Otherwise the matrix forming excipient may be a lipidic substance, such as hydrogenated castor oil, or carnuba wax, incorporated at a level between 10 and 40% by weight with respect to that of the prolonged release tablet.

A Capsule Comprising a Mixture of Prolonged Release Pellets and Immediate Release Pellets.

Immediate release pellets may be prepared by deposition of the drug suspended in water or an organic solvent such as ethanol with hydroxypropylmethylcellulose or povidone or another suitable polymer to act as a binder, onto a spherical granule. A fluid bed coating apparatus is generally used. Particles may be agglomerated to form spherical granules or pellets, in a high speed mixer granulator, or rotary fluid bed agglomerator. These methods are described by K. W. Olson and A. M. Mehta, Int. J. Pharm. Tech &. Prod. Mfr. 6 18-24, 1985. Pellets may be also prepared by extrusion of wet masses or melts followed by spheronisation, for example as described in C. Vervaet, L. Baert & J. P. Remon Int. J. Pharm. 116 (1995) 131-146. Excipients used are typically those with plastic qualities such as microcrystalline cellulose, but also mannitol. Small quantities of a polymeric binder are generally added. Surfactants such as sodium dodecyl sulphate may also be incorporated to give easier extrusion.

Prolonged release pellets are prepared by coating immediate release pellets in the same way as described for the tablets. Coating may be carried out, for example, in coating pans or in fluid bed coater-driers. The amount and composition of the coating is adjusted from that used in the tablet, to reduce the permeability of the coating in order to take into account the far greater surface for diffusion in the pellets.

A Tablet Comprising a Number of Prolonged Release Coated Pellets Comprising the Drug Imbedded in a Matrix Also Comprising the Drug.

Alternatively the tablet may consist of a mixture of prolonged release coated pellets and of immediate release non-coated pellets comprising the drug, imbedded in a drug-free matrix.

Alternatively the prolonged release coated pellets may be furthermore coated with a layer comprising the drug and other excipients allowing immediate release from that layer, imbedded in a drug-free matrix.

The matrix surrounding the pellets should preferably be formulated so that the compression into tablets does not interfere with the integrity of the membrane surrounding the pellets. On contact with fluid the tablet disintegrates, releasing the drug rapidly, from the matrix, or the immediate release pellets, or from the immediate release pellet coating, and then releasing the drug from the prolonged release pellets slowly.

A Multilayer Tablet Comprising: (i) One or Two Prolonged Release Layers, Comprising the Drug and a Hydrophilic Polymer (Preferably a Cellulose Derivative), (ii) One or More Immediate Release Layers Comprising the Drug, and Possibly, (iii) Another Layer not Comprising the Drug, that Modulates Release of the Drug from the Prolonged Release Layer.

In this type of tablet, each layer contains other excipients, so as to give suitable properties for compression, lubrication, binding as is well known to one skilled in the art. Examples of such bilayer and multilayer tablets are shown in FIG. 5a-d, where immediate release layers are designated by i, prolonged release layers by p and layers modulating the release profile by m.

A Multicoated Tablet Comprising: (i) a Core Comprising the Prolonged Release Drug, (ii) a Polymer Coating Layer Giving Slow Release of the Drug from this Core, (iii) a Coating Layer Comprising the Immediate Release Drug which is Released Rapidly or Immediately on Contact of the Dosage Form with Fluid.

In this type of tablet, each portion of the tablet, in particular the inner core, can contain other excipients, so as to give suitable properties for compression, lubrication, and binding as is well known to one skilled in the art. Methods for making both multilayered and multicoated tablets are described by W. C. Gunsel, Compression coated and layer tablets in Pharmaceutical Dosage Forms: Tablets, Vol 1. edited by H. A. Lieberman and L. Lachman, Dekker N.Y. (1980).

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Example 1

Preparation of Bilayer Tablet Containing 4 mg of Carbinoxamine Maleate in an Immediate Release Format, and 120 mg pseudoephedrine in a Prolonged Release Format The theoretical quantitative composition (per unit dose) for Carbinoxamine Maleate 4 mg and Pseudoephedrine HCl 120 mg prolonged release tablet is provided below:

Composition of Layer A: Carbinoxamine Maleate Immediate Release

| Ingredient | mg/Tablet |
| --- | --- |
| Carbinoxamine Maleate | 4 |
| Alcohol 95% | 25 |
| Microcrystalline cellulose | 86.8 |
| Starch | 24 |
| Lactose | 24 |
| Croscarmellose Sodium | 9 |
| Magnesium Stearate | 1 |
| Silicone Dioxide | 0.8 |
| Coloring agent | q.s. |
| Total Weight | 150 mg |

Dissolve Carbinoxamine Maleate in Alcohol 95% completely, then absorbed with Microcrystalline cellulose. Dry the wet powder in oven at 60° C. for about 6 hrs and screen the powder together with rest of excipients (Starch, Lactose, Croscarmellose, Mg. Stearate, Silicone Dioxide, and coloring agent if needed) through 40# mesh. Then, blend the mixture in V-blender or other kind of adequate mixer for 5 to 30 minutes.

Composition of Layer B: Pseudoephedrine HCl Prolonged Release

| Ingredient | mg/Tablet |
| --- | --- |
| Pseudoephedrine HCl | 120 |
| Microcrystalline cellulose | 40 |
| HPMC K100M | 155 |
| Silicone Dioxide | 2 |
| Magnesium Stearate | 3 |
| Total Weight | 320 mg |

Screen Pseudoephedrine HCl, Microcrystalline cellulose, HPMC, Silicone Dioxide and Mg. Stearate through 40# mesh and blend together in V-blender or other kind of adequate mixer for 5 to 30 minutes.

After above mentioned process, compress the Layer A and B powder with rotary bilayer tablet compressing machine with suitable tooling to form bilayer tablets. The tablets may be coated.

Example 2

Dissolution Testing for Carbinoxamine Maleate and Pseudoephedrine Hydrochloride The in vitro dissolution profiles of tablets manufactured according to Example 1 are established using the Apparatus II of the United States Pharmacopoeia. 1 dissolution media is employed: 900 ml 0.1N hydrochloric acid (pH=2) and maintained at 37+/−0.5° C. Stirring is by the paddle method (50 rpm). The percentage dissolved is determined by measurement of UV absorbance at 214 nm (continuous sampling by a peristaltic pump in a closed system). Results are reported in FIG. 6.

Example 3

Pharmacokinetics of Carbinoxamine 4 mg Immediate Release Tablet Under Fasted Conditions A single dose fasted bioavailability study was undertaken using four milligram immediate release carbinoxamine maleate tablets formulated in an immediate release format. Samples were taken over a forty eight hours period after administration of the drug, and the first meal was allowed to be ingested four hours after administration. Plasma concentration results from the test are reported in Table 1; pharmacokinetics of the carbinoxamine are reported in Table 2. Table 3 compares the observed pharmacokinetics from this test to those observed by Stockis et al. in *Arzneim.-Forsch* 1992, 42(12):1478-81, and Stockis et al. in *Arzneim.-Forsch* 1995, 45(9) 1009-1012.

FIG. 1 is a mean plasma concentration-time profile of the carbinoxamine after administering the immediate release tablet in the fasted state from time 0 to time 48 hours. Graph (A) is the linear ordinate; graph (B) is the log-linear ordinate.

TABLE 1

Plasma concentration-time data of carbinoxamine under fasted state.

| Time (h) | 101T | 102T | 103T | T-Mean | SD | CV (%) |
|---|---|---|---|---|---|---|
| 0 | blq | blq | blq | n.d | n.d | n.d |
| 0.5 | 434.78 | 459.42 | 52.04 | 315.41 | 228.42 | 72.4 |
| 1 | 5908.19 | 4949.36 | 1602.38 | 4153.31 | 2260.59 | 54.4 |
| 2 | 6488.14 | 5684.72 | 7046.07 | 6406.31 | 684.35 | 10.7 |
| 3 | 8022.80 | 6592.16 | 6573.21 | 7062.72 | 831.50 | 11.8 |
| 4 | 7860.85 | 6226.91 | 5854.14 | 6647.30 | 1067.36 | 16.1 |
| 5 | 7726.57 | 6649.03 | 5171.89 | 6515.83 | 1282.54 | 19.7 |
| 6 | 7251.86 | 6097.18 | 4362.30 | 5903.78 | 1454.45 | 24.6 |
| 8 | 6849.38 | 5707.15 | 3975.57 | 5510.70 | 1446.94 | 26.3 |
| 12 | 5821.63 | 4387.40 | 2669.29 | 4292.77 | 1578.30 | 36.8 |
| 24 | 2632.77 | 2395.51 | 1405.53 | 2144.60 | 650.96 | 30.4 |
| 36 | 1541.30 | 1516.80 | 1055.79 | 1371.30 | 273.51 | 19.9 |
| 48 | 1102.33 | 1003.18 | 523.37 | 876.29 | 309.63 | 35.3 | blq means concentration below lower limit of qualification;
n.d. means not determined.

TABLE 2

Pharmacokinetic parameters of carbinoxamine administered in fasted state.

| Parameters | $AUC_{0-t}$ (pg/ml * li) | $AUC_{0-\infty}$ (pg/ml * li) | $AUC_{0-t}$ $AUC_{0-\infty}$ | $C_{max}$ (pg/ml) | $T_{max}$ (h) | MRT (h) | $T_{1/2}$ (h) | RSQ |
|---|---|---|---|---|---|---|---|---|
| 101 | 169448.6 | 199836.4 | 84.8 | 8022.80 | 3.00 | 24.71 | 19.10 | 0.9827 |
| 102 | 143427.7 | 171088.0 | 83.8 | 6649.03 | 5.00 | 25.90 | 19.11 | 0.9992 |
| 103 | 98373.8 | 111088.9 | 88.6 | 7046.07 | 2.00 | 21.66 | 16.84 | 0.9443 |
| Mean | 137083.4 | 160671.1 | 85.7 | 7239.30 | 3.33 | 24.09 | 18.35 | 0.9754 |
| SD | 35959.7 | 45281.5 | 2.5 | 706.97 | 1.53 | 2.19 | 1.31 | 0.0282 |
| CV (%) | 26.2 | 28.2 | 2.9 | 9.8 | 45.8 | 9.1 | 7.1 | 2.9 |

TABLE 3

PK data comparison.

| | | Literature 1 | | Literature 2 | | |
|---|---|---|---|---|---|---|
| | Our study Tablet 4 mg | Aqueous solution 8 mg | Retard capsule 8 mg | Aqueous solution 4 mg | Retard capsule 4 mg | Retard capsule SS 4 mg |
| $AUC_{0-t}$ (ng/ml * h) | 137.1[a] | 286[b] 143[d] | 238[b] 119[d] | 64[c] | 57[c] | |
| $AUC_{0-\infty}$ (ng/ml * h) | 160.7 | | | | | 125 |
| $C_{max}$ (ng/ml) | 7.2 | 24 12[d] | 16.9 8.45[d] | 6.5 | 4.5 | 13.5 |
| $T_{max}$ (h) | 3.3 | 3 | 8 | 2.6 | 6.2 | 4.8 |
| $T_{1/2}$ (h) | 18.3 | 10.6 | 14.5 | 15 | 30 | 22 |

SS: steady-state (q12h).
[a]$AUC_{0-8}$
[b]$AUC_{0-24}$
[c]$AUC_{0-5}$
[d]Data were normalized to 4 mg dose.
Literature 1: Arzneim-Forsch/Drug Res, 42 (II), 1478-1481. (1992)
Literature 2: Arzneim-Forsch/Drug Res, 45 (II), 1009-1012. (1995)

Example 4

Pharmacokinetics of Carbinoxamine 4 mg Immediate Release Tablet Under Non-Fasted Conditions A single dose bioavailability study was also undertaken in the non-fasted state using 4 mg immediate release carbinoxamine maleate tablets formulated in an immediate release format. Samples were taken over a forty eight hours period after administration of the drug with heparinized tubes. Breakfast was ingested thirty minutes before administration. Plasma concentration results from the test are reported in Table 4; pharmacokinetics of the carbinoxamine are reported in Table 5.

FIG. 2 is a mean plasma concentration-time profile of carbinoxamine after administering the 4 mg carbinoxamine maleate immediate release tablet in the non-fasted state from time 0 to time 48 hours. Graph (A) is the linear ordinate; graph (B) is the log-linear ordinate. FIG. 3 is an overlay of mean plasma concentration-time profiles of carbinoxamine administered under nonfasted and fasted conditions from time 0 to 48 hours, as reported in Example 3. Graph (A) is an overlay in the linear ordinates for the two conditions; graph (B) is an overlay in the log-linear ordinates for the two conditions.

TABLE 4

Plasma concentration-time data of carbinoxamine under nonfasted state.

| Time (h) | 101T | 102T | 103T | T-Mean | SD | CV (%) |
|---|---|---|---|---|---|---|
| 0 | blq | blq | blq | n.d | n.d | n.d |
| 0.5 | 1190.29 | 1371.47 | 1683.25 | 1415.00 | 249.35 | 17.6 |
| 1 | 5017.55 | 15948.51 | 7208.39 | 9391.48 | 5783.24 | 61.6 |
| 2 | 7279.95 | 18873.34 | 10671.05 | 12274.78 | 5960.76 | 48.6 |
| 3 | 7409.87 | 14981.55 | 9399.33 | 10596.92 | 3925.33 | 37.0 |
| 4 | 8113.91 | 12868.20 | 8891.67 | 9957.93 | 2550.20 | 25.6 |
| 5 | 7450.78 | 11670.11 | 8072.86 | 9064.58 | 2277.79 | 25.1 |
| 6 | 7053.79 | 10649.47 | 7232.44 | 8311.90 | 2026.36 | 24.4 |
| 8 | 6458.92 | 8834.94 | 6258.79 | 7184.22 | 1433.07 | 19.9 |
| 12 | 4676.58 | 7186.93 | 4225.70 | 5363.07 | 1595.52 | 29.8 |
| 24 | 3297.38 | 5400.86 | 2909.31 | 3869.18 | 1340.59 | 34.6 |
| 36 | 2197.69 | 3326.26 | 1826.83 | 2453.59 | 786.58 | 32.1 |
| 48 | 1249.68 | 2616.93 | 1084.70 | 1650.44 | 841.06 | 51.0 | blq means concentration below lower limit of qualification;
n.d. means not determined.

TABLE 5

Pharmacokinetic parameters of carbinoxamine under nonfasted state.

| Parameters | $AUC_{0-1}$ (pg/ml * h) | $AUC_{0-\ldots}$ (pg/ml * h) | $AUC_{0-1}$ $AUC_{0-\ldots}$ | Cmax (pg/ml) | $T_{max}$ (h) | MRT (h) | $T_{1/2}$ (h) | RSQ |
|---|---|---|---|---|---|---|---|---|
| 101 | 175421.8 | 206334.1 | 85.0 | 8113.91 | 4.00 | 25.62 | 17.14 | 0.9911 |
| 102 | 291561.8 | 378244.3 | 77.1 | 18873.34 | 2.00 | 31.69 | 22.95 | 0.9650 |
| 103 | 170055.3 | 196441.4 | 86.6 | 10671.05 | 2.00 | 23.42 | 16.86 | 0.9989 |
| Mean | 212346.3 | 260339.9 | 82.9 | 12552.77 | 2.67 | 26.91 | 18.98 | 0.9850 |
| SD | 68655.1 | 102227.9 | 5.1 | 5621.12 | 1.15 | 4.28 | 3.44 | 0.0178 |
| CV (%) | 32.3 | 39.3 | 6.1 | 44.8 | 43.3 | 15.9 | 18.1 | 1.8 |

Example 5

Steady-State Pharmacokinetics of Carbinoxamine 4 mg Immediate Release Tablet The steady state pharmacokinetics of pseudoephedrine were also investigated for a four mg immediate release carbinoxamine tablet, administered every six, eight and twelve hours. Steady state conditions were modeled using the fasted pharmacokinetic values reported in Example 3, assuming a one-compartment model. The results are reproduced in FIG. 4, wherein the top line reflects Q6h administration; the middle line reflects Q8h administration; the bottom line reflects Q12h administration.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of providing relief from symptoms associated with allergic rhinitis comprising administering a single pharmaceutical dosage form that comprises:
   a) a therapeutically effective amount of carbinoxamine or a pharmaceutically acceptable salt thereof in an immediate release format adapted to release at least 80% of said carbinoxamine or carbinoxamine salt in 60 minutes or less when measured in a type II dissolution apparatus according to the U.S. Pharmacopoeia in 0.1N hydrochloric acid buffer (pH=2) at 37° C.; and
   b) a therapeutically effective amount of a second pharmaceutically acceptable agent selected from a decongestant, an antitussive, an analgesic or an expectorant in a prolonged release format adapted to release no more than 50% of said second agent in 60 minutes or less, and at least 75% of said second agent in eight hours or less, when measure in a type II dissolution apparatus according to the U.S. Pharmacopoeia in 01.N hydrochloric acid buffer (pH=2) at 37° C.;
   wherein said therapeutically effective amounts of said carbinoxamine or carbinoxamine salt and said second agent are sufficient to provide relief from said symptoms for at least twelve hours.

2. The method of claim 1 wherein said dosage form is in the form of a capsule, tablet, multilayer tablet or multicoated tablet.

3. The methods of claim 1 wherein said second agent is pseudoephedrine, phenylephrine, codeine, dihydrocodeine, guaifenesin, aspirin, naproxen, acetaminophen, or ibuprofen, or a pharmaceutically acceptable salt thereof.

4. The method of claim 1 wherein said dosage form is in the form of a tablet comprising first and second layers, wherein said first layer comprises about 4 to about 6 mg of said carbinoxamine or pharmaceutically acceptable salt thereof and said second layer comprises said second agent.

5. The method of claim 1 wherein said carbinoxamine is present as 4 mg of carbinoxamine maleate, and said second agent is present as 120 mg of pseudoephedrine hydrochloride.

6. The method of claim 1 wherein said carbinoxamine or pharmaceutically acceptable salt thereof provides antihistamine and anticholinergic relief for at least about twelve hours.

7. The method of claim 1 wherein said second agent provides symptomatic relief for at least about twelve hours.

8. A method of providing relief from symptoms associated with allergic rhinitis comprising:
   a) administering to a human patient a single pharmaceutical dosage form comprising:
      i) a therapeutically effective amount of carbinoxamine or a pharmaceutically acceptable salt thereof in an immediate release form adapted to release at least 80% of said carbinoxamine or carbinoxamine salt in 60 minutes or less when measured in a type II dissolution apparatus according to the U.S. Pharmacopoeia in 0.1N hydrochloric acid buffer (pH=2) at 37° C.; and
      ii) a therapeutically effective amount of a pharmaceutically acceptable decongestant in a prolonged release format adapted to release no more than 50% of said decongestant in 60 minutes or less, and at least 75% of said decongestant in eight hours or less, when measured in a type II dissolution apparatus according to the U.S. Pharmacopoeia in 0.1N hydrochloric acid buffer (pH=2) at 37°;
   b) twelve hours later, and optionally every twelve hours thereafter for two or more days, administering said pharmaceutical dosage form of step (a) to said human; wherein:
      i) said therapeutically effective amounts of said carbinoxamine or carbinoxamine salt and said decongestant are sufficient to provide relief from said symptoms for at least twelve hours; and
      ii) said carbinoxamine or carbinoxamine salt is present in an amount sufficient to produce a mean carbinoxamine plasma concentration during step (b) of more than 25% greater than the mean carbinoxamine plasma concentration produced during step (a).

9. The method of claim 8, wherein said carbinoxamine of pharmaceutically acceptable salt thereof is present in amount sufficient to produce a mean carbinoxamine plasma concentration during step (b) of more than 50% greater than step (a).

10. The method of claim 8 wherein said dosage form is in the form of a capsule, tablet, multilayer tablet or multicoated tablet.

11. The method of claim 8 wherein said decongestant is pseudoephedrine or phenylephrine or a pharmaceutically acceptable salt thereof.

12. The method of claim 8 wherein said dosage from is in the form of a tablet comprising first and second layers, wherein said first layer comprises from about 4 to about 6 mg of carbinoxamine maleate and said second layer comprises said decongestant.

13. The method of claim 1 wherein said carbinoxamine is present as 4 mg of carbinoxamine maleate, and said decongestant is present as 120 mg of pseudoephedrine hydrochloride.

14. The method of claim 8 wherein said carbinoxamine or pharmaceutically acceptable salt thereof provide antihistamine and anticholinergic relief for at least about twelve hours.

15. The method of claim 8 wherein said decongestant provides decongesting relief for at least about twelve hours.

16. The method of claim 4, 6, 9 or 14, wherein said carbinoxamine or a pharmaceutically acceptable salt thereof is carbinoxamine maleate.

* * * * *